United States Patent [19]

Kunisch et al.

[11] Patent Number: 5,196,441

[45] Date of Patent: Mar. 23, 1993

[54] COMPOUNDS USEFUL AS ANTIMICROBIAL AGENTS

[75] Inventors: Franz Kunisch, Odenthal-Glöbusch; Peter Babczinski, Wuppertal; Dieter Arlt, Cologne; Wilhelm Brandes, Leichlingen; Heinz-Wilhelm Dehne, Monheim; Stefan Dutzmann, Hilden; Manfred Plempel, Haan, all of Fed. Rep. of Germany

[73] Assignee: Bayer Aktiengesellschaft, Leverkusen, Fed. Rep. of Germany

[21] Appl. No.: 777,832

[22] Filed: Oct. 10, 1991

[30] Foreign Application Priority Data

Oct. 20, 1990 [DE] Fed. Rep. of Germany ....... 4033415

[51] Int. Cl.[5] .................... C07D 213/55; A61K 31/44
[52] U.S. Cl. ..................................... 514/357; 546/335
[58] Field of Search .................... 546/335; 514/357

[56] References Cited

U.S. PATENT DOCUMENTS 3,510,492  5/1970  Szmuskovicz et al. ............. 546/335
4,554,277  11/1985  Wong ................................. 514/277
4,673,631  6/1987  Fukumoto et al. ................. 430/110

OTHER PUBLICATIONS

Bulletin of the Chemical Society of Japan, vol. 43, No. 7, Jul. 1970.
Chemical Abstracts, vol. 94, No. 25, Abstract No. 206,191u, Jun. 22, 1981, p. 374.
Washington, Science, vol. 115, p. 84 (1952).

*Primary Examiner*—Alan L. Rotman
*Assistant Examiner*—Zinna N. Davis
*Attorney, Agent, or Firm*—Sprung, Horn, Kramer & Woods

[57] ABSTRACT

There are described new 2-cyclohexan-1-yl-amine derivatives of formula (I)

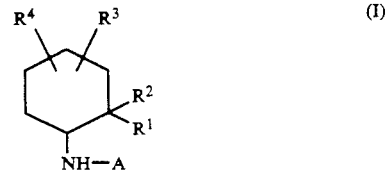

in which A, $R^1$, $R^2$, $R^3$ and $R^4$ have the meaning given in the description, and processes for their preparation.

The compounds of the formula (I) are used as antimicrobial agents.

7 Claims, No Drawings

COMPOUNDS USEFUL AS ANTIMICROBIAL AGENTS

The present invention relates to the use of substituted 2-cyclohexan-1-yl-amine derivatives, some of which are known, as antimicrobial agents in plant protection, mainly as fungicides and as antimycotics, as well as new substituted 2-cyclohexan-1-yl-amine derivatives, and a plurality of processes for their preparation.

It is already known that certain tetrahydrophthalimides such as, for example, cis-N-[(trichloromethyl)thio]-4-cyclohexene-1,2-dicarboimide, have fungicidal properties (cf. for example, Science, (Washington) 115. 84 (1952); U.S. Pat. No. 2,553,770).

However, the action of these compounds is not always entirely satisfactory in all fields of application, in particular when small amounts and low concentrations are applied.

Furthermore, it is also already known that 2-cycloalkenylamine derivatives and their salts, such as, for example N-2-cyclohexen-1-yl-2,2-dimethyl-propionamide, have fungicidal properties (cf. EP-OS (European Published Specification) 0,128,006).

It has now been found that the substituted 2-cyclohexan1-yl-amine derivatives, some of which are known, of the formula (I)

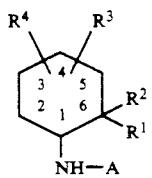

in which

R$^1$ represents hydrogen, halogen or alkyl,

R$^2$ represents formyl, hydroxyalkyl, or one of the radicals

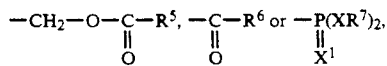

R$^3$ and R$^4$ are identical or different and in each case represent hydrogen, alkyl, alkoxy, or represent unsubstituted or substituted aryl, or represent unsubstituted or substituted aralkyl, or represent unsubstituted or substituted heteroaryl or alkoxyalkyloxy, R$^5$ represents alkyl or alkoxy, R$^6$ represents hydroxyl, hydroxyalkyloxy, halogenoalkyloxy, alkoxy, alkoxyalkyloxy, in each case unsubstituted or substituted alkenylalkyloxy, alkinylalkyloxy and cycloalkyloxy, unsubstituted or substituted aralkyloxy, unsubstituted or substituted aryloxy, unsubstituted or substituted aralkyl, alkylthio, unsubstituted or substituted arylthio, or represents a group —OM, —NR$^8$R$^9$ or —O—Z—NR$^8$R$^9$, R$^7$ represents hydrogen or alkyl, R$^8$ represents hydrogen, alkyl or unsubstituted or substituted aryl, R$^9$ represents hydrogen, alkyl or unsubstituted or substituted aryl, M represents hydrogen, or represents an equivalent of a corresponding alkali metal cation, alkaline earth metal cation or ammonium cation, X and X$^1$ are identical or different and represent oxygen or sulphur, A represents hydrogen or an amino protective group, and Z represents a straight-chain or branched alkyl chain, and their acid addition salts and metal salt complexes have powerful biological properties.

The compounds of the formula (I) contain 1 to 4 centres of chirality and can therefore exist in various mixtures of enantiomers and diastereomers which, if desired, can be separated in the customary fashion. The invention also claims the use of the pure enantiomers and diastereomers as well as the use of the mixtures.

For simplicity's sake, the following text will always mention the use of compounds of the formula (I), even though this is understood as meaning the pure compounds as well as the mixtures with various proportions of isomeric, enantiomeric and diastereomeric compounds.

Surprisingly, the substituted 2-cyclohexan-1-yl-amine derivatives of the formula (I), some of which are known, and their acid addition salts and metal salt complexes have outstanding fungicidal properties when applied in appropriate concentrations. In addition, the substituted 2-cyclohexan-1-yl-amine derivatives of the formula (I), some of which are known, also have very good antimicrobial properties when applied in appropriate concentrations.

Formula (I) provides a general definition of the substituted 2-cyclohexan-1-yl-amine derivatives to be used according to the invention.

Unless defined otherwise, the meanings in the general formulae in the following text are:

Alkyl - straight-chain or branched alkyl having 1 to 8, preferably 1 to 6, in particular 1 to 4, carbon atoms. The following may be mentioned by way of example and as preferred: optionally substituted methyl, ethyl, n.- and i.-propyl and n-, i-, s- and t-butyl.

Alkoxy - unsubstituted or substituted, straight-chain or branched alkoxy having 1 to 8, preferably 1 to 6, in particular 1 to 4, carbon atoms. The following may be mentioned by way of example and as preferred: optionally substituted methoxy, ethoxy, n.- and i.-propoxy and n-, i-, s- and t-butoxy.

Aryl - preferably unsubstituted or substituted phenyl or naphthyl, in particular phenyl.

Aralkyl and aralkoxy - aralkyl or aralkoxy, each of which has preferably 6 or 10, in particular 6, carbon atoms in the aryl moiety (preferably phenyl or naphthyl, in particular phenyl) and preferably 1 to 8, in particular 1 to 6, carbon atoms in the alkyl moiety, it being possible for the alkyl moiety to be straight-chain or branched, and each of which is unsubstituted or substituted in the aryl moiety and/or alkyl moiety. The following may be mentioned by way of example and as preferred: optionally substituted benzyl and phenylethyl, or benzyloxy and phenylethyloxy, respectively.

Unsubstituted or substituted heterocyclic radicals in the general formulae denote heteroaromatic 5-6-membered rings having preferably 1 to 3, in particularly 1 or 2, identical or different hetero atoms. Hetero atoms are oxygen, sulphur or nitrogen. The following may be mentioned by way of example and as preferred: pyrrolidinyl, piperidinyl, furyl, thienyl, pyrazolyl, imidazolyl, 1,2,3- and 1,2,4-triazolyl, oxazolyl, isoxazolyl, thiazolyl, isothiazolyl, 1,3,4- and 1,2,4-oxadiazolyl, azepinyl, pyrrolyl, isopyrrolyl, pyridyl, pyridazinyl, pyrimidinyl, pyrazinyl and 1,2,3-, 1,2,4-, 1,2,5- and 1,3,4-thiadiazolyl.

Halogen in the general formulae preferably denotes fluorine, chlorine, bromine and iodine, in particular fluorine, chlorine and bromine, and particularly preferably fluorine and chlorine.

The optionally substituted radicals of the general formulae can carry one or more, preferably 1 to 3, in particular 1 or 2, identical or different substituents. Examples of preferred substituents which may be mentioned are:

Alkyl having preferably 1 to 4, in particular 1 or 2, carbon atoms, such as methyl, ethyl, n.- and i.-propyl and n.-, i.- and t.-butyl; alkoxy having preferably 1 to 4, in particular 1 or 2, carbon atoms, such as methoxy, ethoxy, n.- and i.-propyloxy and n.-, i.-, sec.- and t.-butyloxy; alkylthio having preferably 1 to 4, in particular 1 or 2, carbon atoms, such as methylthio, ethylthio, n.- and i.-propylthio and n.-, i.-, sec.- and t.-butylthio; halogenoalkyl, halogenoalkoxy and halogenoalkylthio, each of which has preferably 1 to 4, in particular 1 or 2, carbon atoms and preferably 1 to 9, in particular 1 to 5. halogen atoms, the halogen atoms being identical or different and preferably being fluorine, chlorine or bromine, in particular fluorine, such as trifluoromethyl, trifluoromethoxy and trifluoromethylthio; hydroxyl; halogen, preferably fluorine, chlorine, bromine and iodine, in particular fluorine, chlorine and bromine; cyano; nitro; amino; dialkylamino having preferably 1 to 4, in particular 1 or 2, carbon atoms per alkyl group, such as methyl-ethyl-amino, and methyl-n.-butylamino; carboxyl.

Preferred compounds of the formula (I) which are used are those in which $R^1$ represents hydrogen, halogen and straight-chain or branched alkyl having 1 to 6 carbon atoms, $R^2$ represents formyl, straight-chain or branched hydroxyalkyl having 1 to 8 carbon atoms in the alkyl moiety, or represents one of the radicals

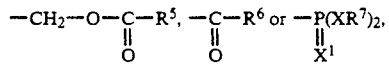

$R^3$ and $R^4$ are identical or different and in each case represent hydrogen, in each case straight-chain or branched alkyl or alkoxy having 1 to 8 carbon atoms, alkoxyalkyloxy having 1 to 8 carbon atoms in each of the individual alkyl moieties, or represent aryl or aralkyl, each of which has 6 to 10 carbon atoms in the aryl moiety and if appropriate 1 to 4 carbon atoms in the alkyl moiety, and each of which is unsubstituted or monosubstituted to pentasubstituted in the aryl moiety by identical or different substituents, suitable aryl substituents being: halogen, nitro, cyano, amino, $C_1$–$C_4$-alkyl, $C_1$–$C_4$-alkoxy or $C_1$–$C_4$-alkylthio, halogeno-($C_1$–$C_4$)-alkyl, halogeno-($C_1$–$C_4$)-alkoxy, halogeno-($C_1$–$C_4$)-alkylthio, each of which has 1 to 9 identical or different halogen atoms, and di-($C_1$–$C_4$)-alkylamino; furthermore represents a heteroarylic 5- or 6-membered ring which is unsubstituted or monosubstituted to pentasubstituted by identical or different substituents and which can contain 1 to 3 oxygen, sulphur and/or nitrogen atoms as further hetero atoms, suitable substituents for the heterocycle in each case being: halogen, nitro, cyano, amino, $C_1$–$C_4$-alkyl, $C_1$–$C_4$-alkoxy, $C_1$–$C_4$-alkylthio, halogeno($C_1$–$C_4$)-alkyl, halogeno-($C_1$–$C_4$)-alkoxy, halogeno($C_1$–$C_4$)-alkylthio, each of which has 1 to 9 identical or different halogen atoms, and di-($C_1$–$C_4$)-alkylamino, $R^5$ represents in each case straight-chain or branched alkyl or alkoxy having 1 to 6 carbon atoms, $R^6$ represents hydroxyl, straight-chain or branched hydroxyalkyloxy, having 1 to 8 carbon atoms, straight-chain or branched halogenoalkyloxy having 1 to 8 carbon atoms and 1 to 17 identical or different halogen atoms, or represents alkenylalkyloxy, alkinylalkyloxy and cycloalkyloxy, each of which has 3 to 6 carbon atoms, and each of which is unsubstituted or monosubstituted to polysubstituted by identical or different halogen substituents, or represents in each case straight-chain or branched alkoxy or alkylthio having 1 to 6 carbon atoms, straight-chain or branched alkoxyalkyloxy having 1 to 6 carbon atoms in the alkoxy and alkyl moieties, or represents aryloxy, arylthio, aralkyl or aralkyloxy, each of which has 6 to 10 carbon atoms in the aryl moiety and if appropriate 1 to 8 carbon atoms in the alkyl moiety and each of which is unsubstituted or monosubstituted to pentasubstituted in the aryl moiety by identical or different substituents, suitable aryl substituents being the aryl substituents mentioned under $R^3$, or represents a group —OM, —NR$^8$R$^9$ or —O—Z—NR$^8$R$^9$, $R^7$ represents hydrogen or straight-chain or branched alkyl having 1 to 6 carbon atoms, $R^8$ and $R^9$ are identical or different and represent hydrogen, straight-chain or branched alkyl having 1 to 6 carbon atoms, or aryl which has 6 to 10 carbon atoms and which is unsubstituted or monosubstituted to pentasubstituted by identical or different substituents, suitable aryl substituents being the aryl substituents mentioned under $R^3$, M represents hydrogen, or represent an equivalent of a corresponding alkali metal cation, alkaline earth metal cation or ammonium cation, X and $X^1$ are identical or different and represent oxygen or sulphur, A represents hydrogen or an amino protective group, and Z represents a straight-chain or branched alkyl chain having 1 to 8 carbon atoms.

Other compounds preferably to be used according to the invention are also addition products of acids and those substituted 2-cyclohexan-1-yl-amine derivatives of the formula (I) in which $R^1$, $R^2$, $R^3$ and $R^4$ have those meanings which have already been mentioned in connection with the description of the substances to be used according to the invention as being preferred for these substituents.

The acids which can be added on preferably include hydrohalic acids such as, for example, hydrochloric acid and hydrobromic acid, in particular hydrochloric acid, furthermore phosphoric acid, nitric acid, mono- and bifunctional carboxylic acids and hydroxycarboxylic acids such as, for example, acetic acid, trifluoroacetic acid, maleic acid, succinic acid, fumaric acid, tartaric acid, citric acid, salicylic acid, sorbic acid and lactic acid, oleic acid, stearic acid, or benzoic acid which is optionally monosubstituted to polysubstituted by nitro or halogen, or gluconic acid, ascorbic acid, malic acid, sulphamic acid, sulphonic acids such as, for example, p-toluenesulphonic acid, 1,5-naphthalenedisulphonic acid and methanesulphonic acid, and also imides such as, for example, phthalimide, saccharin and thiosaccharin.

Other compounds to be preferably used according to the invention are furthermore addition products of salts of metals of main group I, II and III and of tin, also furthermore salts of metals of sub-group I, II, VII and VIII of the Periodic Table of the Elements and those substituted 2-cyclohexan-1-yl-amine derivatives of the formula (I) in which $R^1$, $R^2$, $R^3$ and $R^4$ have the meanings which have already been mentioned in connection with the description of the substances of the formula (I) to be used according to the invention as being preferred for these substituents.

In this context, salts of copper, zinc, manganese, magnesium, calcium, tin, iron, cobalt and of nickel are particularly preferred. Suitable anions of these salts are those which are derived from those acids which lead to physiologically acceptable addition products. Acids of this type which are particularly preferred in this connection are the hydrohalic acids such as, for example, hydrochloric acid and hydrobromic acid, further phosphoric acid, nitric acid and sulphuric acid.

Compounds of the formula (I) which are particularly preferably used are those in which $R^1$ represents hydrogen, fluorine, chlorine, bromine or straight-chain or branched alkyl having 1 to 4 carbon atoms, $R^2$ represents formyl, straight-chain or branched hydroxyalkyl having 1 to 4 carbon atoms in the alkyl moiety, or represents one of the radicals

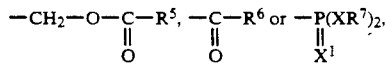

$R^3$ and $R^4$ are identical or different and in each case represent hydrogen, in each case straight-chain or branched alkyl or alkoxy having 1 to 6 carbon atoms, alkoxyalkyloxy having 1 to 6 carbon atoms in each of the individual alkyl moieties, or represent phenyl or phenylalkyl, having, where appropriate, 1 or 2 carbon atoms in the alkyl moiety, each of which is unsubstituted or monosubstituted to pentasubstituted in the phenyl moiety by identical or different substituents, suitable phenyl substituents being: fluorine, chlorine, bromine, nitro, cyano, amino, $C_1$-$C_2$-alkyl, $C_1C_3$-alkoxy or $C_1$-$C_2$-alkylthio, halogeno($C_1$-$C_2$)-alkyl, halogeno-($C_1$-$C_2$)-alkoxy and halogeno($C_1$-$C_2$)-alkylthio, each of which has 1 to 5 identical or different fluorine and/or chlorine atoms, furthermore represent a heterocyclic five- or six-membered group from the series comprising furyl, thienyl, pyrrolyl, pyrazolyl, imidazolyl, 1,2,3- or 1,2,4-triazolyl, oxazolyl, isoxazolyl, 1,2,4- or 1,3,4-oxadiazolyl, thiazolyl, isothiazolyl, 1,2,3-, 1,2,4-, 1,2,5- or 1,3,4-thiadiazolyl, pyridyl, pyridazinyl, pyrimidinyl and pyrazinyl, each of which is, if appropriate, bonded via a methylene group and each of which is unsubstituted or monosubstituted to trisubstituted by identical or different substituents, suitable substituents for the heterocycle in each case being: fluorine, chlorine, bromine, nitro, cyano, amino, $C_1$-$C_2$-alkyl, $C_1$-$C_2$-alkoxy or $C_1$-$C_2$-alkylthio, halogeno-($C_1$-$C_2$)-alkyl, halogeno-($C_1$ -$C_2$)-alkoxy, halogeno-($C_1$-$C_2$)-alkylthio each of which has 1 to 5 identical or different fluorine and/or chlorine atoms, and di-($C_1$-$C_2$)-alkylamino, $R^5$ represents in each case straight-chain or branched alkyl or alkoxy having 1 to 4 carbon atoms, $R^6$ represents hydroxyl, straight-chain or branched hydroxylalkyloxy having 1 to 6 carbon atoms, straight-chain or branched halogenoalkyloxy having 1 to 6 carbon atoms and 1 to 13 identical or different halogen atoms, or represents alkenylalkyloxy, alkinylalkyloxy and cycloalkyloxy, having 3 to 6 carbon atoms and each of which is unsubstituted or monosubstituted to trisubstituted by identical or different substituents from the series comprising fluorine, chlorine and bromine, or represents in each case straight-chain or branched alkoxy or alkylthio having 1 to 4 carbon atoms, or straight-chain or branched alkoxyalkyloxy having 1 to 4 carbon atoms in each of the alkoxy or alkyl moieties, or represents phenyloxy, phenylthio, phenylalkyl or phenylalkyloxy, having, where appropriate, 1 to 6 carbon atoms in the alkyl moiety, each of which is unsubstituted or monosubstituted to pentasubstituted in the phenyl moiety by identical or different substituents, suitable phenyl substituents being the phenyl substituents mentioned under $R^3$, or represents a group —OM, —NR$^8$R$^9$ or —O—Z—NR$^8$R$^9$, $R^7$ represents hydrogen or straight-chain or branched alkyl having 1 to 4 carbon atoms, $R^8$ and $R^9$ are identical or different and represent hydrogen, straight-chain or branched alkyl having 1 to 4 carbon atoms, or phenyl which is unsubstituted or monosubstituted to pentasubstituted by identical or different substituents, suitable phenyl substituents being the phenyl substituents mentioned under $R^3$, M represents hydrogen, or represents an equivalent of a corresponding sodium cation, potassium cation or ammonium cation, X and $X^1$ are identical or different and represent oxygen or sulphur, A represents hydrogen or an amino protective group and Z represents a straight-chain or branched alkyl chain having 1 to 6 carbon atoms.

The term "amino protective group" is generally known and relates to groups which are suitable for protecting (blocking) an amino group from chemical reactions, but which are readily detachable after the desired reaction has been carried out at different sites of the molecule. Typical representatives of such groups are, in particular, unsubstituted or substituted acyl groups, aryl groups, for example DNP (2,4-dinitrophenyl), aralkoxymethyl groups, for example BOM (N-(benzyloxy)methyl) or aralkyl groups (for example benzyl, 4-nitrobenzyl or triphenylmethyl). Since the amino protective groups are removed after the desired reaction (or reaction sequence), their nature and size is usually not crucial; however, those having 1 - 20, in particular 1 - 8, carbon atoms are preferred. The term "acyl group" in connection with the present invention must be seen in the broadest sense. It embraces acyl groups which are derived from aliphatic, araliphatic, aromatic or heterocyclic carboxylic acids or sulphonic acids, and, in particular alkoxycarbonyl, aryloxycarbonyl, and mainly aralkoxycarbonyl groups. Examples of acyl groups of this type are alkanoyl such as acetyl, propionyl, butyryl; aralkanoyl such as phenylacetyl; aroyl such as benzoyl or toluyl; aryloxyalkanoyl such as POA (phenoxyacetyl); alkoxycarbonyl such as methoxycarbonyl, ethoxycarbonyl, 2,2,2-trichloroethoxycarbonyl, BOC (tert.-butoxycarbonyl), 2-iodoethoxycarbonyl; aralkyloxycarbonyl such as CBZ ("carbobenzoxy") and 4-methoxybenzyloxycarbonyl. Preferred amino protective groups are benzyl, acetyl, methoxycarbonyl, allyloxycarbonyl, trichloroethyloxycarbonyl, (±)-menthyloxycarbonyl, tert-butoxycarbonyl and benzyloxycarbonyl.

Another subject of the application are new substituted 2-cyclohexan-1-yl-amine derivatives of the formula (Ia)

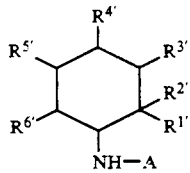

in which
R$^{1'}$ represents hydrogen, halogen or alkyl,
R$^{2'}$ represents formyl, hydroxyalkyl, or represents one of the radicals

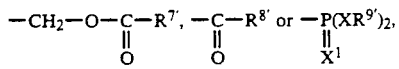

R$^{3'}$, R$^{4'}$, R$^{5'}$ and R$^{6'}$ are identical or different and in each case represent hydrogen, alkyl or alkoxy, or represent unsubstituted or substituted aryl, or represent unsubstituted or substituted aralkyl, or represent unsubstituted or substituted heteroaryl or alkoxyalkyloxy,
where at least two of the radicals R$^{3'}$, R$^{4'}$, R$^{5'}$ or R$^{6'}$ represent hydrogen,
R$^{7'}$ represents alkyl or alkoxy
R$^{8'}$ represents hydroxyl, hydroxyalkyloxy, halogenoalkyloxy, alkoxy, alkoxyalkyloxy, in each case unsubstituted or substituted alkenylalkyloxy, alkinylalkyloxy and cycloalkyloxy, unsubstituted or substituted aralkyloxy, unsubstituted or substituted aryloxy, unsubstituted or substituted aralkyl, alkylthio, unsubstituted or substituted arylthio, or represents a group —O—Z—NR$^{10'}$R$^{11'}$, —NR$^{10'}$R$^{11'}$ or —OM,
R$^{9'}$ represents hydrogen or alkyl
R$^{10'}$ and R$^{11'}$ are identical or different and in each case represent hydrogen, alkyl or unsubstituted or substituted aryl,
Z represents a straight-chain or branched alkyl chain and
A represents hydrogen or an amino protective group,
M represents hydrogen, or represents an equivalent of a corresponding alkali metal cation, alkaline earth metal cation or ammonium cation and
X and X$^1$ are identical or different and represent oxygen or sulphur,
and their acid addition salts and metal salt complexes, with the exception of compounds in which A, R$^{3'}$, R$^{4'}$, R$^{5'}$ and R$^{6'}$ represent hydrogen, R$^{2'}$ represents carboxyl and R$^{2'}$ represents methyl.

Formula (Ia) provides a general definition of the substituted 2-cyclohexan-1-yl-amine derivatives which were hitherto unknown.

Preferred compounds of the formula (Ia) are those in which
R$^{1'}$ represents hydrogen, halogen or straight-chain or branched alkyl having 1 to 6 carbon atoms,
R$^{2'}$ represents formyl, straight-chain or branched hydroxyalkyl having 1 to 8 carbon atoms in the alkyl moiety, or represents one of the radicals

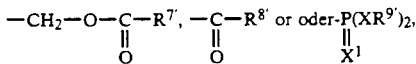

R$^{3'}$, R$^{4'}$, R$^{5'}$ and R$^{6'}$ are identical or different and in each case represent hydrogen, in each case straight-chain or branched alkyl or alkoxy having 1 to 8 carbon atoms, alkoxyalkyloxy having 1 to 8 carbon atoms in each of the individual alkyl moieties, or represent aryl or aralkyl, each of which has 6 to 10 carbon atoms in the aryl moiety and if appropriate 1 to 4 carbon atoms in the alkyl moiety and each of which is unsubstituted or monosubstituted to pentasubstituted in the aryl moiety by identical or different substituents, suitable aryl substituents being: halogen, nitro, cyano, amino, C$_1$-C$_4$-alkyl, C$_1$-C$_4$-alkoxy, C$_1$-C$_4$-alkylthio, halogeno-(C$_1$-C$_4$)-alkyl, halogeno-(C$_1$-C$_4$)-alkoxy, halogeno-(C$_1$-C$_4$)-alkylthio, each of which has 1 to 9 identical or different halogen atoms, and di-(C$_1$-C$_4$)-alkylamino, furthermore represent a heterocyclic 5- or 6-membered group from the series comprising furyl, thienyl, pyrrolyl, pyrazolyl, imidazolyl, 1,2,3- or 1,2,4-triazolyl, oxazolyl, isoxazolyl, 1,2,4- or 1,3,4-oxadiazolyl, thiazolyl, isothiazolyl, 1,2,3-, 1,2,4-, 1,2,5- or 1,3,4-thiadiazolyl, pyridyl, pyridazinyl, pyrimidinyl and pyrazinyl, each of which is bonded, if appropriate, via a methylene group and each of which is unsubstituted or monosubstituted to trisubstituted by identical or different substituents, suitable substituents for the heterocycle in each case being: halogen, nitro, cyano, amino, C$_1$-C$_4$-alkyl, C$_1$-C$_4$-alkoxy or C$_1$-C$_4$-alkylthio, halogeno(C$_1$-C$_4$)-alkyl, halogeno-(C$_1$-C$_4$)-alkoxy or halogeno(C$_1$-C$_4$)-alkylthio, each of which has 1 to 9 identical or different halogen atoms, and di-(C$_1$-C$_4$)-alkylamino,
where at least two of the radicals R$^{3'}$, R$^{4'}$, R$^{5'}$ or R$^{6'}$ represent hydrogen,
R$^{7'}$ represents in each case straight-chain or branched alkyl or alkoxy having 1 to 6 carbon atoms,
R$^{8'}$ represents hydroxyl, straight-chain or branched hydroxyalkyloxy having 1 to 8 carbon atoms, straight-chain or branched halogenoalkyloxy having to 8 carbon atoms and 1 to 17 identical or different halogen atoms, or represents alkenylalkyloxy, alkinylalkyloxy and cycloalkyloxy, each of which has 3 to 6 carbon atoms and each of which is unsubstituted or monosubstituted to polysubstituted by identical or different halogen substituents, in each case straight-chain or branched alkoxy or alkylthio having 1 to 6 carbon atoms, or straight-chain or branched alkoxyalkyloxy having 1 to 6 carbon atoms in each of the alkoxy or alkyl moieties, or represents aryloxy, arylthio, aralkyl or aralkyloxy, each of which has 6 to 10 carbon atoms in the aryl moiety and if appropriate to 8 carbon atoms in the alkyl moiety and each of which is unsubstituted or monosubstituted to pentasubstituted in the aryl moiety by identical or different substituents, suitable aryl substituents being the aryl substituents mentioned above, or represents a group —O—Z—NR$^{10'}$R$^{11'}$, —NR$^{10'}$R$^{11'}$ or —OM,
R$^{9'}$ represents hydrogen or straight-chain or branched alkyl having 1 to 6 carbon atoms,
R$^{10'}$ and R$^{11'}$ are identical or different and represent hydrogen, straight-chain or branched alkyl having 1 to 6 carbon atoms, or aryl which has 6 to 10 carbon atoms and which is unsubstituted or monosubstituted to pentasubstituted by identical or different substituents, suitable aryl substituents being the aryl substituents mentioned above,
M represents hydrogen or represents an equivalent of a corresponding alkali metal cation, alkaline earth metal cation or ammonium cation and
Z represents a straight-chain or branched alkyl chain having 1 to 8 carbon atoms, A represents hydrogen or an amino protective group, and X and $X^1$ are identical or different and represent oxygen or sulphur, with the exception of compounds in which $R^{3'}$, $R^{4'}$, $R^{5'}$, $R^{6'}$ and A represent hydrogen, $R^{2'}$ represents carboxyl and R represents methyl.

Other preferred compounds according to the invention are addition products of acids and those substituted 2-cyclohexan-1-yl-amine derivatives of the formula (Ia) in which $R^{1'}$, $R^{2'}$, $R^{3'}$, $R^{4'}$, $R^{5'}$ and $R^{6'}$ have the above-mentioned meanings.

Other compounds according to the invention are those having the following formula:

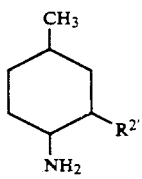

in which $R^{2'}$ represents the grouping

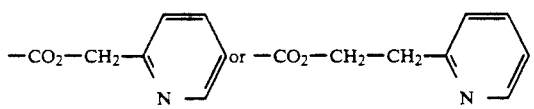

or an acid addition salt or metal said complex thereof.

The acids which can be added on preferably include hydrohalic acids such as, for example, hydrochloric acid and hydrobromic acid, in particular hydrochloric acid, furthermore phosphoric acid, nitric acid, mono- and bifunctional carboxylic acids and hydroxycarboxylic acids such as, for example, acetic acid, trifluoroacetic acid, maleic acid, succinic acid, fumaric acid, tartaric acid, citric acid, salicylic acid, sorbic acid and lactic acid, oleic acid, stearic acid, or benzoic acid which is optionally monosubstituted or polysubstituted by nitro or halogen, or gluconic acid, ascorbic acid, malic acid, sulphamic acid, sulphonic acids such as, for example, p-toluenesulphonic acid, 1,5-naphthalenedisulphonic acid and methanesulphonic acid, and also imides such as, for example, phthalimide, saccharin and thiosaccharin.

Other compounds to be preferably used according to the invention are furthermore addition products of salts of metals of main groups I, II and III and of tin, furthermore salts of metals of sub-groups I, II, VII and VIII of the Periodic Table of the Elements and those substituted 2-cyclohexan-1-yl-amine derivatives of the formula (Ia) in which $R^{1'}$, $R^{2'}$, $R^{3'}$, $R^{4'}$, $R^{5'}$ and $R^{6'}$ have the abovementioned meanings.

In this context, salts of copper, zinc, manganese, magnesium, calcium, tin, iron, cobalt and of nickel are particularly preferred. Suitable anions of these salts are those which are derived from those acids which lead to physiologically acceptable addition products. Acids of this type which are particularly preferred in this connection are the hydrohalic acids such as, for example, hydrochloric acid and hydrobromic acid, further phosphoric acid, nitric acid and sulphuric acid.

Particularly preferred compounds of the formula (Ia) are those in which $R^{1'}$ represents straight-chain or branched alkyl having 1 to 4 carbon atoms or in particular hydrogen, $R^{2'}$ represents formyl, straight-chain or branched hydroxyalkyl having 1 to 4 carbon atoms in the alkyl moiety, or represents one of the radicals

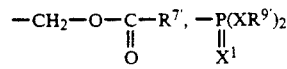

or, in particular

$R^{3'}$, $R^{4'}$, $R^{5'}$ and $R^{6'}$ are identical or different and in each case represent hydrogen, in each case straight-chain or branched alkyl or alkoxy having 1 to 6 carbon atoms, alkoxyalkyloxy having 1 to 6 carbon atoms in each of the individual alkyl moieties, or represent phenyl or phenylalkyl, having, where appropriate, 1 or 2 carbon atoms in the alkyl moiety, each of which is unsubstituted or monosubstituted to trisubstituted in the phenyl moiety by identical or different substituents, suitable phenyl substituents being: fluorine, chlorine, bromine, nitro, cyano, amino, $C_1$-$C_2$-alkyl, $C_1$-$C_3$-alkoxy or $C_1$-$C_2$-alkylthio, halogeno-($C_1$-$C_2$)-alkyl, halogeno-($C_1$-$C_2$)-alkoxy and halogeno-($C_1$-$C_2$)-alkylthio, each of which has 1 to 5 identical or different fluorine and/or chlorine atoms, and di-($C_1$-$C_2$)-alkylamino, furthermore represent a heterocyclic five- or six-membered group from the series comprising furyl, thienyl, pyrrolyl, pyrazolyl, imidazolyl, 1,2,3- or 1,2,4-triazolyl, oxazolyl, isoxazolyl, 1,2,4- or 1,3,4-oxadiazolyl, thiazolyl, isothiazolyl, 1,2,3-, 1,2,4-, 1,2,5- or 1,3,4-thiadiazolyl, pyridyl, pyridazinyl, pyrimidinyl and pyrazinyl, each of which is, if appropriate, bonded via a methylene group and each of which is unsubstituted or monosubstituted to trisubstituted by identical or different substituents, suitable substituents for the heterocycle in each case being: fluorine, chlorine, bromine, nitro, cyano, amino, $C_1$-$C_2$-alkyl, $C_1$-$C_2$-alkoxy or $C_1$-$C_2$-alkylthio, halogeno-($C_1$-$C_2$)-alkyl, halogeno-($C_1$-$C_2$)-alkoxy, halogeno-($C_1$-$C_2$)-alkylthio, each of which has 1 to 5 identical or different fluorine and/or chlorine atoms and di-($C_1$-$C_2$)-alkylamino, —but in particular in each case represent hydrogen or in each case straight-chain or branched alkyl having 1 to 4 carbon atoms— where at least two of the radicals $R^{3'}$, $R^{4'}$, $R^{5'}$ and $R^{6'}$ represent hydrogen, $R^{7'}$ in each case represents straight-chain or branched alkoxy or in particular alkyl having 1 to 4 carbon atoms, $R^{8'}$ represents hydroxyl, straight-chain or branched hydroxyalkyloxy having 1 to 6 carbon atoms, straight-chain or branched halogenoalkyloxy having 1 to 6 carbon atoms and 1 to 13 identical or different halogen atoms, or represents alkenylalkyloxy, alkinylalkyloxy and cycloalkyloxy, each of which has 3 to 6 carbon atoms and each of which is unsubstituted or monosubstituted to trisubstituted by identical or different substituents from the series comprising fluorine, chlorine and bromine, or represents in each case straight-chain or branched alkoxy or alkylthio having 1 to 4 carbon atoms, straight-chain or branched alkoxyalkylalkoxy having 1 to 4 carbon atoms in each of the alkoxy or alkyl moieties, or represents phenyloxy, phenylthio, phenylalkyl or phenylalkyloxy, each of which has, if appropriate, 1 to 6 carbon atoms in the alkyl moiety and each of which is unsubstituted or monosubstituted to trisubstituted in the phenyl moiety by identical or different substituents, suitable phenyl substituents being the phenyl substituents mentioned above, or represents a group —O—Z—NR$^{10'}$R$^{11'}$, —NR$^{10'}$R$^{11'}$ or —OM, —but in particular represents hydroxyl, in each case straight-chain or branched alkoxy, alkoxyalkyloxy or phenylalkoxy, each of which has 1 to 4 carbon atoms in the alkoxy or alkyl moiety—

R$^{9'}$ represents hydrogen or straight-chain or branched alkyl having 1 to 4 carbon atoms, R$^{10'}$ and R$^{11'}$ are identical or different and represent hydrogen, straight-chain or branched alkyl having 1 to 4 carbon atoms, or represent phenyl which is unsubstituted or monosubstituted to trisubstituted by identical or different substituents, suitable phenyl substituents being the phenyl substituents mentioned above, M represents hydrogen, or represents an equivalent of a corresponding alkali metal cation, alkaline earth metal cation or ammonium cation and Z represents a straight-chain or branched alkyl chain having 1 to 6 carbon atoms.

A represents hydrogen or an amino protective group, and

X and X$^1$ are identical or different and represent oxygen or sulphur, with the exception of compounds A, R$^{3'}$, R$^{4'}$, R$^{5'}$ and R$^{6'}$ represent hydrogen, R$^{2'}$ represents carboxyl and R$^{1'}$ represents methyl.

The acid addition salts and metal salt complexes to be mentioned in this connection are those which have already been mentioned in the description of the preferred 2-cyclohexen-1-yl-amine derivatives of the formula (Ia) which were substituted according to the invention.

The substituted 2-cyclohexan-1-yl-amine derivatives of the formula (Ia) are obtained when A) 2-cyclohexan-1-yl-amine derivatives of the formula (II)

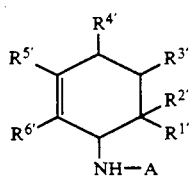

(II)

or

B) phenylamine derivatives of the formula (III)

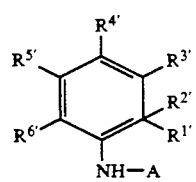

(III)

in which

R$^{1'}$, R$^{2'}$, R$^{3'}$, R$^{4'}$, R$^{4'}$, R$^{6'}$ and A in each case have the abovementioned meaning and are hydrogenated in a generally customary manner with hydrogen at temperatures from 10° C. to 300° C. and pressures from 10 to 300 bar, if appropriate in the presence of a diluent such as, for example, ethanol, dimethoxyethanol or tetrahydrofuran, and in the presence of a catalyst such as, for example, ruthenium/carbon or rhodium on aluminium oxide.

The substituted 2-cyclohexan-1-yl-amine derivatives of the formula (Ia) in which A represents hydrogen are furthermore obtained C) from the 2-cyclohexane derivatives of the formula (Ia)

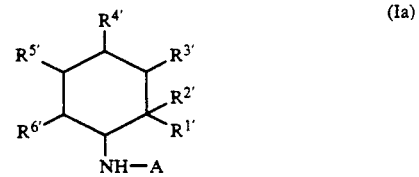

(Ia)

in which

R$^{1'}$, R$^{2'}$, R$^{3'}$, R$^{4'}$, R$^{5'}$ and R$^{6'}$ have the abovementioned meaning and A represents an amino protective group in a manner known per se by customary methods, for example by solvolysis, such as hydrolysis, acidolysis, by reduction such as, for example, by hydrogenolysis in the presence of a hydrogenation catalyst or by means of a reduction system comprising metal and proton-eliminating agetn, where, depending on the nature of the protective group, various types (also other types) of elimination methods, also selective elimination methods, can be used, if appropriate in the presence of a suitable solvent or diluent or a mixture of these, the process being carried out, if required, with cooling, at room temperature or with heating, for example, in a temperature range from about −10° C. to the boiling point of the reaction medium, preferably from about −10° C. about 150° C., and, if necessary, in a sealed vessel, under pressure, in an inert gas atmosphere and/or under anhydrous conditions, and, if desired, the resulting products are converted into acid addition salts or metal salt complexes (cf. Protective Groups in Organic Synthesis, Th. W. Greene, Wiley Interscience, 1981).

The formyl, acetyl or 2,2,2-trichloroacetyl group which has been mentioned, amongst others, as amino protective group, can be eliminated for example by hydrolysis.

The hydrolysis is effected in a manner known per se with the aid of water, this process being carried out advantageously in the presence of an acid or base which aids hydrolysis, if appropriate in the presence of an inert solvent or diluent, and/or with cooling or heating.

Examples of possible acids are inorganic acids such as mineral acids, for example sulphuric acid, phosphoric acid or hydrohalic acids, organic carboxylic acids such as lower alkanecarboxylic acids, for example glacial acetic acid, such as optionally unsaturated dicarboxylic acids, for example oxalic, malonic, maleic or fumaric acid, or such as hydroxycarboxylic acids, for example tartaric acid or citric acid, or sulphonic acids, such as C$_1$-C$_7$-alkane- or optionally substituted benzenesulphonic acid, for example methane- or p-toluenesulphonic acid.

Examples of suitable bases are hydroxides, hydrides, amides, alkanolates, carbonates, triphenylmethylides, di-C$_1$-C$_7$-alkylamides, amino-C$_1$-C$_7$-alkylamides or C$_1$-C$_7$-alkylsilylamides of alkali metals, or naphthaleneamines, C$_1$-C$_7$-alkylamines, basic heterocycles, ammonium hydroxides, and also carbocyclic amines. Examples which may be mentioned are lithium hydroxide, sodium hydroxide, sodium hydride, sodium amide, sodium ethylate, potassium tert-butylate, potassium carbonate, lithium triphenylmethylide, lithium diisopropylamide, potassium 3-(aminopropyl)amide, potassium bis-(trimethylsilyl)-amide, dimethyl-aminonaphthalene, di- or triethylamine, pyridine, benzyl-trimethyl-ammonium hydroxide, 1,5-diazabicyclo[4.3.0]non-5-ene (DBN) and also 1,8-diaza-bicyclo[5.4.0]undec-7-ene (DBU).

The acidolysis can be carried out successfully, for example using strong acids, advantageously trifluoroacetic acid or perchloric acid, but also other strong inorganic acids such as hydrochloric acid or sulphuric acid, strong organic carboxylic acids such as trichloroacetic acid, or sulphonic acids such as benzene- or p-toluene sulphonic acid. It is possible for an additional inert solvent to be present. Preferred inert solvents which are suitable are organic solvents, for example carboxylic acids such as acetic acid, ethers such as tetrahydrofuran or dioxane, amides such as dimethylformamide (DMF), halogenated hydrocarbons such as dichloromethane, and furthermore also alcohols such as methanol, ethanol or isopropanol, and also water.

Mixtures of the abovementioned solvents are also suitable. Trifluoroacetic acid is preferably used in excess without adding a further solvent, perchloric acid is preferably used in the form of a mixture of acetic acid and 70% strength perchloric acid in a ratio of 9:1. The reaction temperatures for these solvolyses are advantageously between about 0° and about 50° C., the process is preferably carried out between 15° and 30° C. (room temperature).

For example, the BOC group can preferably be eliminated using 40% strength trifluoroacetic acid in methylene chloride, or approximately 3 to 5N hydrochloric acid in dioxane at 15°-30° C., and the FMOC group (9-fluorenylmethyloxycarbonyl) using an approximately 5 to 20% strength solution of dimethylamine, diethylamine or piperidine in dimethylformamide, at 15°-30° C. The DNP group (2,4-dinitrophenyl) can also be eliminated successfully for example using an approximately 3 to 10% strength solution of 2-mercaptoethanol in dimethylformamide/water, at 15°-30° C. Protective groups which can be detached by means of hydrogenolysis (for example BOM, CBZ or benzyl) can be eliminated for example by treatment with hydrogen in the presence of a catalyst (for example a noble-metal catalyst such as palladium, expediently on a support such as charcoal). Suitable solvents in this context are the solvents mentioned above, in particular for example alcohols, such as methanol or ethanol, or amides, such as dimethylformamide. As a rule, the hydrogenolysis is carried out at temperatures from about 0° to 100° C. and a pressure from about 1 to 200 bar, preferably 20° to 30° C. and 1 to 10 bar. For example, hydrogenolysis on the CBZ group is carried out successfully on 5 to 10% Pd/charcoal in methanol at 20°-30° C.

Examples of amino protective groups which are eliminated by means of a reducing system of metal and protoneliminating agent are (4-nitro)-benzyloxycarbonyl, 2-iodo- or 2,2,2-trichloroethoxycarbonyl or phenacyloxycarbonyl.

The metal component of the metallic reducing system is, for example, a base metal, such as alkali metal or alkaline earth metal, for example lithium, sodium, potassium, magnesium or calcium, or a transition metal, for example zinc, tin, iron or titanium, while suitable proton-eliminating agents are, for example, protonic acids of the type mentioned above, such as hydrochloric acid or acetic acid, $C_1$-$C_7$-alcohols, such as ethanol, and/or amines or ammonia. Examples of such systems are sodium/ammonia, zinc/hydrochloric or acetic acid, or zinc/ethanol.

Furthermore, 4-nitrobenzyloxycarbonyl can be split, for example, with a dithionite, such as sodium dithionite, phenacyloxycarbonyl and 2-halogeno-$C_2C_7$-alkanoyl, for example with the aid of a nucleophilic reagent, such as a thiolate, for example sodium thiophenolate, or thiourea and base, followed by hydrolysis, and allyl or but-2-enyl with the aid of a rhodium(III) halide, such as rhodium-(III) chloride.

The compounds of the formula (I) which are known can be prepared analogously to the new compounds of the formula (Ia).

If, for example, tert.-butyl (6-carbomethoxy-4-methyl-2-cyclohexen-1-yl)-carbonate, are used as starting substances, the course of the reaction of preparation process (A) can be illustrated by the following equation:

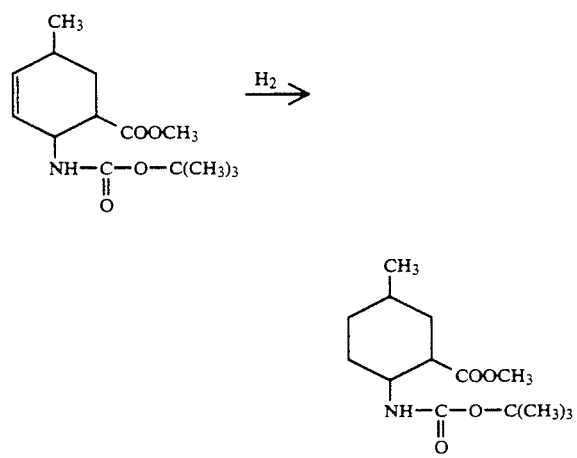

If, for example, tert-butyl (4-methyl-2-carbomethoxycyclohexan-1-yl)carbamate and 1N sodium hydroxide solution are used as starting substances in a first step and 1N hydrochloric acid in a second step, the course of the reaction of the preparation process (C) can be illustrated by the following equation:

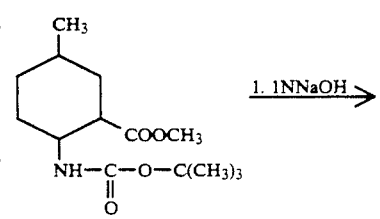

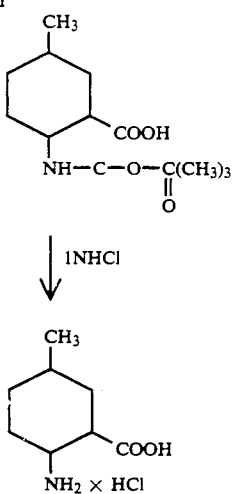

Formula (II) and formula (III) provide general definitions of the 2-cyclohexen-1-yl-amine derivatives and the phenylamine derivatives, respectively, required as starting substances for carrying out preparation process (A). In this formula (II) or formula (III), $R^{2'}$, $R^{3'}$, $R^{4'}$, $R^{5'}$ and $R^{6'}$ and $R^{1'}$ in formula (II) preferably, or in particular, represent the substituents which have been mentioned above in the description of the new 2-cyclohexan-1-yl-amine derivatives of the formula (Ia) as being preferred, or particularly preferred, for these radicals.

The 2-cyclohexen-1-yl-amine derivatives of the formula (II) and the phenylamine derivatives of the formula (III) are known and can be prepared in a simple, analogous manner by known processes.

Processes A and B according to the invention for the preparation of the new cyclohexane derivatives of the formula (Ia) are preferably carried out using diluents.

Suitable diluents for this purpose are virtually all inert organic solvents. These preferably include aliphatic and aromatic, optionally halogenated hydrocarbons such as pentane, hexane, heptane, cyclohexane, petroleum ether, benzine, ligroin, benzene, toluene, xylene, methylene chloride, ethylene chloride, chloroform, carbon tetrachloride, chlorobenzene and o-dichlorobenzene, ethers such as diethyl ether and dibutyl ether, glycol dimethyl ether and diglycol dimethyl ether, tetrahydrofuran and dioxane, and also dimethyl sulphoxide, tetramethylene sulphone and hexamethylphosphoric triamide.

Suitable inert gases for this purpose are nitrogen and virtually all noble gases, in particular argon.

When carrying out processes A and B for the preparation of the 2-cyclohexane derivatives of the formula (Ia), the reaction temperatures can be varied within a substantial range. In general, the process is carried out at temperatures between 10° C. and 300° C., preferably between 20° C. and 150° C.

For carrying out processes A and B for the preparation of the 2-cyclohexane derivatives of the formula (Ia), hydrogen is employed in excess and 0.1 to 5.0 moles of catalyst are preferably employed.

The process according to the invention for the preparation of 2-cyclohexane derivatives of the formula (Ia) is generally carried out under increased pressure. In general, the process is carried out under a pressure from 1 to 300 bar, preferably at 5 to 200 bar.

Suitable catalysts for the preparation of the new 2-cyclohexan-1-yl-carboxylic acid derivatives of the formula (Ia) in accordance with process variants A and B are catalysts which are customary for reactions of this type; noble-metal catalysts such as, for example, ruthium on carbon or rhodium on aluminium oxide are preferably used.

However, under certain conditions, the process for the preparation of the new 2-cyclohexane derivatives of the formula (Ia) can also be carried out without diluents and a pressure from 1 to 200 bar.

In general, the reactions are carried out in a suitable diluent, and the reaction mixture is stirred for several hours at the particular temperature required. Working-up is carried out in each case by customary methods. In general, the procedure is followed in which the reaction mixture is either concentrated under reduced pressure or poured into water, and the product is isolated by extraction or filtration and purified by chromatography.

The compounds of the formula (I), and (Ia) can be obtained as mixtures of enantiomers or diastereomers.

The invention embraces the pure isomers as well as the mixtures. These mixtures of diastereomers can be separated into the components following conventional methods, for example by selective crystallisation, from suitable solvents or chromatography on silica gel or aluminium oxide. Racemates can be resolved by customary methods to give the individual enantiomers, for example by salt formation with optically active acids such as camphorsulphonic acid or dibenzoyltartaric acid and selective crystallisation, or by derivatisation with suitable optically active reagents, separation of the diastereomeric derivatives, and recleavage or separation on optically active column material.

Suitable acids for the preparation of acid addition salts of the compounds of the formula (Ia) are preferably those which have already been mentioned in connection with the description of the acid addition salts according to the invention as being preferred acids.

The acid addition salts of the compounds of the formula (Ia) can be obtained in a simple manner by customary salt formation methods, for example by dissolving a compound of the general formula (Ia) in a suitable inert solvent and adding the acid, for example hydrochloric acid, and they can be isolated in a customary manner, for example by filtration, and, if appropriate, purified by washing with an inert organic solvent.

Suitable salts of metals for the preparation of metal salt complexes of the compounds of the general formula (Ia) are preferably those which have already been described further above.

The metal salt complexes of compounds of the general formula (Ia) can be obtained in a simple manner by customary processes, for example by dissolving the metal salt in alcohol, for example ethanol, and adding the solution to compounds of the general formula (Ia). Metal salt complexes can be isolated in a customary manner, for example by filtration, and, if appropriate, purified by recrystallisation.

The active compounds of the formulae (I) and (Ia) which can be used according to the invention and their acid addition salts have a powerful biological action and can be employed in practice for combating undesired pests. For example, the active compounds can be employed for use as plant protection agents, especially as fungicides.

Fungicidal agents in plant protection are employed for combating Plasmodiophoromycetes, Oomycetes, Chytridiomycetes, Zygomycetes, Ascomycetes, Basidiomycetes and Deuteromycetes.

Some causative organisms of fungal and bacterial diseases which come under the generic names listed above may be mentioned as examples, but not by way of limitation:

Xanthomonas species, such as, for example, *Xanthomonas campestris pv. oryzae;*

Pseudomonas species, such as, for example, *Pseudomonas syringae pv. lachrymans;*

Erwinia species, such as, for example, *Erwinia amylovora;*

Pythium species, such as, for example, *Pythium ultimum;*

Phytophthora species, such as, for example, *Phytophthora infestans;*

Pseudoperonospora species, such as, for example, *Pseudoperonospora humuli* or *Pseudoperonospora cubensis;*

Plasmopara species, such as, for example, *Plasmopara viticola;*

Peronospora species, such as, for example, *Peronospora pisi* or *P. brassicae;*

Erysiphe species, such as, for example, *Erysiphe graminis;*

Sphaerotheca species, such as, for example, *Sphaerotheca fuliginea;*

Podosphaera species, such as, for example, *Podosphaera* leucotricha;

Venturia species, such as, for example, *Venturia inaequalis;*

Pyrenophora species, such as, for example, *Pyrenophora teres* or *P. graminea* (conidia form: Drechslera, syn: Helminthosporium);

Cochliobolus species, such as, for example, *Cochliobolus sativus* (conidia form: D echslera, syn: Helminthosporium);

Uromyces species, such as, for example, *Uromyces* appendiculatus;

Puccinia species, such as, for example, *Puccinia* recondita;

Tilletia species, such as, for example, *Tilletia caries;*

Ustilago species, such as, for example, *Ustilago nuda* or *Ustilago avenae;*

Pellicularia species, such as, for example, *Pellicularia* sasakii;

Pyricularia species, such as, for example *Pyricularia* oryzae;

Fusarium species, such as, for example, *Fusarium* culmorum;

Botrytis species, such as, for example, *Botrytis cinerea;*

Septoria species, such as, for example, *Septoria nodorum;*

Leptosphaeria species, such as, for example, *Leptosphaeria nodorum;*

Cercospora species, such as, for example, *Cercospora canescens;*

Alternaria species, such as, for example, *Alternaria brassicae* and

Pseudocercosporella species, such as, for example, *Pseudocercosporella herpotrichoides.*

The good toleration, by plants, of the active compounds, at the concentrations required for combating plant diseases, permits treatment of above-ground parts of plants, of vegetative propagation stock and seeds, and of the soil.

As plant protection agents, the active compounds which can be used according to the invention can be employed with particularly good success protectively, for combating Phytophthora species on tomatoes and Venturia species in apples.

Moreover, some of the active compounds which can be used according to the invention have a good action against Pythium species, Alternaria species and Cercospora species.

Depending on their particular physical and/or chemical properties, the active compounds which can be used according to the invention can be converted into customary formulations, such as solutions, emulsions, suspensions, powders, foams, pastes, granules, aerosols, very fine capsules in polymeric substances and in coating compositions for seed, as well as ULV cold-mist and warm-mist formulations.

These formulations are produced in a known manner, for example by mixing the active compounds with extenders, that is, liquid solvents, liquefied gases under pressure, and/or solid carriers, optionally with the use of surface-active agents, that is, emulsifying agents and/or dispersing agents and/or foam-forming agents. In the case of the use of water as an extender, organic solvents can, for example, also be used as auxiliary solvents. As liquid solvents, there are suitable in the main: aromatics, such as xylene, toluene, or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water; by liquefied gaseous extenders or carriers are meant liquids which are gaseous at ambient temperature and under atmospheric pressure, for example aerosol propellants, such as halogenated hydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly-disperse silica, alumina and silicates; as solid carriers for granules there are suitable: for example crushed and fractionated natural minerals such as calcite, marble, pumice, sepiolite and dolomite, as well as synthetic granules of inorganic and organic meals, and granules of organic material such as sawdust, coconut shells, maize cobs and tobacco stalks; as emulsifying and/or foam-forming agents there are suitable: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as albumen hydrolysis products; as dispersing agents there are suitable: for example lignin-sulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5 and 90%.

The active compounds which can be used according to the invention, as such or in their formulations, can also be used for combating weeds as mixtures with known herbicides, finished formulations or tank mixes being possible.

Mixing with other known active compounds, such as fungicides, insecticides, acaricides, nematicides, bird repellants, plant nutrients and agents which improve the soil structure, is also possible.

The active compounds can be used as such, in the form of their formulations or in the use forms prepared therefrom by further dilution, such as ready-to-use solutions, suspensions, emulsions, powders, pastes and granules. They are applied in the customary manner, for example by watering, spraying, atomising or scattering.

The active compounds which can be used according to the invention can be applied before or after emergence of the plants.

They can also be incorporated into the soil before sowing.

The amount of active compound used can vary within a substantial range. It depends essentially on the nature of the desired effect. In general, the application rates are between 0.01 and 10 kg of active compound per hectare of soil area, preferably between 0.05 and 5 kg per ha.

Furthermore, the compounds of the formulae (I) and (Ia) which can be used according to the invention and their acid addition salts have antimicrobial, in particular powerful antibacterial and antimycotic, actions. They have a very broad antimycotic spectrum of action, in particular against dermatophytes and yeasts as well as biphasic fungi, for example against Candida species such as *Candida albicans*, Epidermophyton species such as *Epidermophyton floccosum*, Aspergillus species such as *Aspergillus niger* and *Aspergillus fumigatus*, Trichophyton species such as *Trichophyton mentagrophytes*, Microsporon species such as *Microsporon felineum* as well as Torulopsis species such as *Torulopsis glabrata*. The enumeration of these microorganisms in no case represents a limitation of the microorganisms which can be combated, but is of illustrative character.

Examples of indications in human medicine which may be mentioned are: dermatomycoses and systemic mycoses caused by *Trichophyton mentagrophytes* and other Trichophyton species, Microsporon species as well as *Epidermophyton floccosum*, yeasts and biphasic fungi, as well as moulds.

Indication areas which may be mentioned for example in veterinary medicine are: All dermatomycoses and systemic mycoses, in particular those caused by the abovementioned pathogens.

The present invention includes pharmaceutical preparations which contain, besides non-toxic inert pharmaceutically suitable excipients, one or more active compounds according to the invention, or which consist of one or more active compounds according to the invention.

The present invention also includes pharmaceutical preparations in dosage units. This means that the preparations are in the form of individual portions, for example tablets, coated tablets, capsules, pills, suppositories and ampoules, whose active compound content corresponds to a fraction, or a multiple, of an individual dose. The dosage units may contain, for example, 1, 2, 3 or 4 individual doses or ½, ⅓ or ¼ of an individual dose. An individual dose preferably contains the amount of active compound which is administered in one application and which usually corresponds to a whole, a half or a third or a quarter of a daily dose.

Non-toxic, inert pharmaceutically suitable excipients are understood as meaning solid, semi-solid or liquid diluents, fillers or formulation auxiliaries of any type.

Preferred pharmaceutical preparations which may be mentioned are tablets, coated tablets, capsules, pills, granules, suppositories, solutions, suspensions and emulsions, pastes, ointments, gels, creams, lotions, powders or sprays.

Tablets, coated tablets, capsules, pills and granules can contain the active substance, or active substances, besides the customary excipients such as (a) fillers and extenders, for example starches, lactose, sucrose, glucose, mannitol and silicare, (b) binders, for example carboxymethylcellulose, alginates, gelantine, polyvinylpyrrolidone, (c) humectants, for example glycerol, (d) disintegrants, for example agar-agar, calcium carbonate and sodium bicarbonate, (e) solution retardants, for example paraffin, and (f) absorption accelerators, for example quaternary ammonium compounds, (g) wetting agents, for example cetyl alcohol or glycerol monostearate, (h) adsorbents, for example kaolin and bentonite, and (i) lubricants, for example talc, calcium stearate and magnesium stearate, and solid polyethylene glycols, or mixtures of the substances mentioned under (a) to (i).

The tablets, coated tablets, capsules, pills and granules may be provided with the customary optional opacifying agent-containing coatings and shells and may be composed in such a way that they release the active compound, or preferably, in a particular part of the intestinal tract, in which case for example polymeric substances and waxes can be used as embedding materials.

If appropriate, the active compound, or active compounds, may also be present in microencapsulated form with one or more of the abovementioned excipients.

Suppositories may contain the customary water-soluble or water-insoluble excipients, for example polyethylene glycols, fats, for example cocoa fat, and higher esters (for example $C_{14}$-alcohol with $C_{16}$-fatty acid) or mixtures of these substances, in addition to the active compound, or active compounds.

Ointments, pastes, creams and gels may contain the customary excipients in addition to the active compound or active compounds, for example animal and vegetable fats, waxes, paraffins, starch, tragacanth, cellulose derivatives, polyethylene glycols, silicones, bentonites, silica, talc and zinc oxide or mixtures of these substances.

Powders and sprays may contain the customary excipients, for example lactose, talc, silica, aluminium hydroxide, calcium silicate and polyamide powder or mixtures of these substances, besides the active compound or active compounds, and sprays may additionally contain the customary propellants, for example chlorofluorohydrocarbons.

Solutions and emulsions may contain, besides the active compound or active compounds, the customary excipients such as solvents, solution retardants and emulsifiers, for example water, ethyl alcohol, isopropyl alcohol, ethyl carbonate, ethyl acetate, benzyl alcohol, benzyl benzoate, propylene glycol, 1,3-butylene glycol, dimethylformamide, oils, in particular cottonseed oil, groundnut oil, maize germ oil, olive oil, castor oil and sesame oil, glycerol, glycerolformal, tetrahydrofurfuryl alcohol, polyethylene glycols and fatty acid esters of sorbitan, or mixtures of these substances.

For parenteral administration, the solutions and emulsions may also be present in sterile and blood-isotonic form.

Suspensions may contain, besides the active compound or active compounds, the customary excipients such as liquid diluents, for example water, ethyl alcohol, propyl alcohol, suspending agents, for example ethoxylated isostearyl alcohols, polyoxyethylene sorbitol esters and polyoxyethylene sorbitan esters, microcrystalline cellulose, aluminium metahydroxide, bentonite, agar-agar and tragacanth, or mixtures of these substances.

The said formulation forms may also contain colorants, preservatives and odour-improving and flavour-improving additives, for example peppermint oil and eucalyptus oil, and sweeteners, for example saccharin.

The therapeutically active compounds should preferably be present in the abovementioned pharmaceutical preparations in a concentration of about 0.1 to 99.5, preferably from 0.5 to 95% by weight, of the total mixture.

Besides the active compounds according to the invention, the abovementioned pharmaceutical preparations may also contain further pharmaceutical active compounds.

The abovementioned pharmaceutical preparations are produced in a customary manner by known methods, for example by mixing the active compound or active compounds, with the excipient or the excipients.

The present invention also includes the use of the active compounds according to the invention and also of pharmaceutical preparations containing one or more active compounds according to the invention, in human and veterinary medicine for the prophylaxis, improvement and/or cure of the abovementioned diseases.

The active compounds or the pharmaceutical preparations can be administered locally, orally, parenterally, intraperitoneally and/or rectally, preferably parenterally, in particular intravenously.

In general, it has proved advantageous both in human and in veterinary medicine to administer the active compound or active compounds according to the invention in total amounts of about 2.5 to about 200, preferably 5 to 150, mg/kg of body weight every 24 hours, if appropriate in the form of several individual doses, to obtain the desired results.

In the case of oral administrations, the active compounds according to the invention are administered in total amounts of about 2.5 to about 200, preferably 5 to 150 mg/kg of body weight every 24 hours, and in the case of parenteral administration in total amounts of about 2.5 to about 50, preferably 1 to 25 mg/kg of body weight every 24 hours.

However, it may be necessary to deviate from the said dosages, depending on the species and the body weight of the subject to be treated, the nature and severity of the disease, the type of preparation, and the application of the medicament, and also the period or interval within which the administration takes place. For example, in some cases it may be sufficient to manage with less than the abovementioned amount of active compound, while in other cases the amount of active compound indicated above must be exceeded. The optimum dosage required in each case and the type of administration of the active compounds can easily be established by anyone skilled in the art on the basis of his expert knowledge.

The preparation and the use of the active compounds according to the invention can be seen from the examples which follow.

PREPARATION EXAMPLES

Example 1 (Process A)

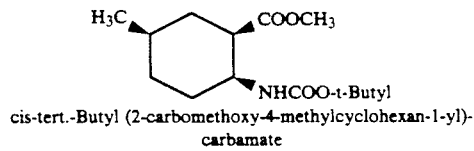

cis-tert.-Butyl (2-carbomethoxy-4-methylcyclohexan-1-yl)-carbamate

A solution of 30 g (0.11 mol) of cis-tert.-butyl (4-methyl-6-carbomethoxy-2-cyclohexen-1-yl)-carbamate in 100 ml of ethanol is hydrogenated at room temperature and 30 bar $H_2$ until hydrogen uptake is complete. The catalyst is filtered off, the filtrate is evaporated to dryness, and 28 g (93% of theory) of cis-tert.-butyl (2-carbomethoxy-4-methylcyclohexan-1-yl)-carbamate having a melting point of 74°–79° C. are obtained.

Example 2

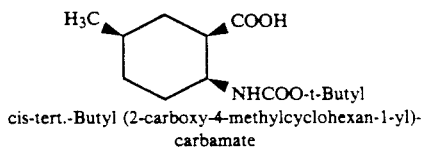

cis-tert.-Butyl (2-carboxy-4-methylcyclohexan-1-yl)-carbamate 15 g (0.055 mol) of cis-tert.-butyl (2-carbomethoxy-4-methyl-2-cyclohexen-1-yl)-carbamate which have been ground finely in a mortar are suspended in 60 ml of 1N sodium hydroxide solution and the suspension is stirred for 20 hours at 50° C. After cooling, the mixture is extracted once with diethyl ether, a pH of 1 is established in the aqueous phase at 0° C. using concentrated hydrochloric acid, and the solid is filtered off with suction. After washing with water and drying, 13.3 g (94% of theory) of cis-tert.-Butyl (2-carboxy-4-methylcyclohexan-1-yl)-carbamate having a melting point of 184°–188° C. are obtained.

Example 3 (Process C)

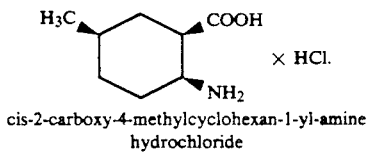

cis-2-carboxy-4-methylcyclohexan-1-yl-amine hydrochloride 5 g (0.02 mol) of cis-tert.-butyl (2-carboxy-4-methylcyclohexan-1-yl)-carbamate are suspended in 20 ml of 1N hydrochloric acid and the suspension is stirred for 12 hours at 55° to 60° C. After evaporation and drying in high vacuum, 3.7 g (96% of theory) of cis-2-carboxy-4-methylcyclohexan-1-yl-amine hydrochloride are obtained as a white solid having a melting point of 218°–230° C.

Example 4 (Process B)

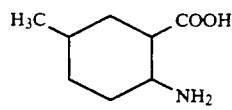

2-Carboxy-4-methylcyclohexan-1-yl-amine 50 g (0.33 mol) of 2-amino-5-methyl-benzoic acid, dissolved in 100 ml of tetrahydrofuran, are hydrogenated for 14 hours at 200° C. and 200 bar hydrogen in the presence of 5 g of ruthenium/charcoal. After cooling and evaporation, 30 g of 2-carboxy-4-methyl-cyclohexan-1-yl-amine are obtained as a pale oil.

$^1$H NMR (200 MHz, CDCl$_3$): $\delta$=0.85–0.98 (m, 3H); 1.05–2.00 (m, 9H); 2.35–2.68 (m, 1H).

Example 5

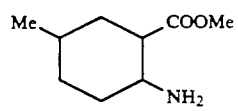

2-Carboxymethyl-4-methyl-cyclohexan-1-yl-amine 7.3 ml (0.1 mol) of thionyl chloride are added to 30 ml of methanol at −5° C. under N$_2$, and 15 g (0.096 mol) of 2-carboxy-4-methylcyclohexan-1-yl-amine in 10 ml of methanol are then added dropwise to this solution at 0° C. After the mixture ha been stirred under reflux for 12 hours it is cooled, a further 10 ml of methanol and 3 ml (0.04 mol) of thionyl chloride are added, and stirring under reflux is continued for 4 hours. After cooling and evaporation to dryness, 5 g of the residue is taken up in about 50 ml of diethyl ether and the mixture is washed in about 100 ml of cold 1N Naton lye and water. The organic phase is dried and concentrated. 3.5 g (85% of theory) of 2-carboxymethyl-4-methyl-cyclohexan-1-yl-amine are obtained as a pale yellow oil.

$^1$H NMR (200 MHz, CDCl$_3$): $\delta$=3.70 (s, 3H, -CO$_2$CH$_3$).

The end products of the formula (Ia)

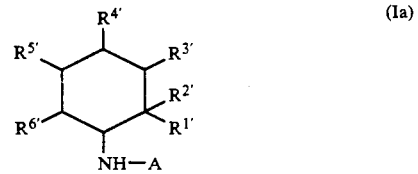

(Ia)

listed in Table 1 below are obtained analogously to the methods described in Example to 5 and taking into consideration the information in the description of the processes according to the invention.

| Example No. | A | R$^{1'}$ | R$^{2'}$ | R$^{3'}$ | R$^{4'}$ | R$^{5'}$ | R$^{6'}$ | physical constant |
|---|---|---|---|---|---|---|---|---|
| 6 | H × HCl | H | CO$_2$H | H | C$_2$H$_5$ | H | H | m.p.: 203° C. |
| 7 | H × HCl | H | CO$_2$H | H | H | CH$_3$ | H | m.p. 183–237° C. (isomer mixture) |
| 8 | H | H | CO$_2$H | H | CH$_3$ | H | H | cis isomer |
| 9 | H × Cu(OCOCH$_3$)$_2$ | H | CO$_2$H | H | CH$_3$ | H | H | cis isomer |
| 10 | H × HSO$_3$CH$_3$ | H | CO$_2$H | H | CH$_3$ | H | H | cis isomer |
| 11 | H × p-tolulsulphonic acid | H | CO$_2$H | H | CH$_3$ | H | H | cis isomer |
| 12 | H × HNO$_3$ | H | CO$_2$H | H | CH$_3$ | H | H | cis isomer |
| 13 | H × HBF$_4$ | H | CO$_2$H | H | CH$_3$ | H | H | cis isomer |
| 14 | H × CH$_2$(COOH)$_2$ | H | CO$_2$H | H | CH$_3$ | H | H | cis isomer |
| 15 | H × HO$_2$C—CO$_2$H | H | CO$_2$H | H | CH$_3$ | H | H | cis isomer |
| 16 | H × saccharin | H | CO$_2$H | H | CH$_3$ | H | H | cis isomer |
| 17 | H × Na | H | CO$_2$H | H | CH$_3$ | H | H | cis isomer |
| 18 | H × NH$_3$ | H | CO$_2$H | H | CH$_3$ | H | H | cis isomer |
| 19 | H | H | CO$_2$—CH$_2$—C$_6$H$_5$ | H | CH$_3$ | H | H | cis isomer |
| 20 | H | H | CO$_2$—CH$_2$—(2-pyridyl) | H | CH$_3$ | H | H | cis isomer |
| 21 | H | H | CO$_2$—(CH$_2$)$_2$—(2-pyridyl) | H | CH$_3$ | H | H | cis isomer |
| 22 | H | H | CO$_2$—(CH$_2$)$_2$—C$_6$H$_5$ | H | CH$_3$ | H | H | cis isomer |
| 23 | H | H | CO$_2$—CH(CH$_3$)$_2$ | H | CH$_3$ | H | H | cis isomer |
| 24 | H × HCl | H | CO$_2$CH$_3$ | H | CH$_3$ | H | H | cis isomer |

-continued

| Example No. | A | $R^{1'}$ | $R^{2'}$ | $R^{3'}$ | $R^{4'}$ | $R^{5'}$ | $R^{6'}$ | physical constant |
|---|---|---|---|---|---|---|---|---|
| 25 | H × HCl | H | CO₂—CH₂—C₆H₅ (benzyl) | H | CH₃ | H | H | cis isomer |
| 26 | H × HCl | H | CO₂—CH₂—(2-pyridyl) | H | CH₃ | H | H | cis isomer |
| 27 | H × HCl | H | CO₂—(CH₂)₂—(2-pyridyl) | H | CH₃ | H | H | cis isomer |
| 28 | H × HCl | H | CO₂—(CH₂)₂—C₆H₅ | H | CH₃ | H | H | cis isomer |
| 29 | H × HCl | H | CO₂—CH(CH₃)₂ | H | CH₃ | H | H | cis isomer |
| 30 | H × CF₃—CO₂H | H | CO—S—CH₂CO₂C₂H₅ | H | CH₃ | H | H | isomer mixture |
| 31 | H × CF₃—CO₂H | H | CO—S—C₆H₅ | H | CH₃ | H | H | isomer mixture |
| 32 | H × HCl | H | CO₂Me | H | CH₃ | H | H | isomer mixture |
| 33 | H × CF₃—CO₂H | H | CO—NH—CH(CH₃)—CO₂C₂H₅ | H | CH₃ | H | H | isomer mixture |
| 34 | H × HCl | H | CO₂H | H | CH₃ | H | H | (−)-Enantiomer |
| 35 | H × HCl | H | CO₂H | H | CH₃ | H | H | (+)-Enantiomer $[\alpha]_D = +53,2$ (C = 1; H₂C) |
| 36 | H × HCl | H | CO₂Et | H | CH₃ | H | H | cis isomer |
| 37 | H | H | CO₂CH₂—C≡CH | H | CH₃ | H | H | cis isomer |
| 38 | COCH₃ | H | CO₂H | H | CH₃ | H | H | cis isomer Fp.: 216° C. |
| 39 | COCH(NH₂)CH₃ | H | CO₂H | H | CH₃ | H | H | cis isomer |
| 40 | H × HCl | H | CO₂H | H | H | C₂H₅ | H | Fp.: 206–30° C. |
| 41 | H | H | CO₂H | H | CH₃ | H | H | $[\alpha]_D = 38.9$ (C = 1; H₂O) |

Preparation of the Starting Compounds

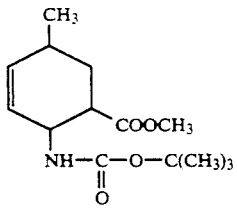

(II)

A solution of 10 g (0.05 mol) of methyl 2-carboxy-5-methylcyclohex-3-ene-carboxylate and 8 g (0.062 mol) of N,N-diisopropylethylamine in 30 ml of acetone is treated at −5° C. in the course of 30 minutes with a solution of 5.4 g (0.05 mol) of ethyl chloroformate in 15 ml of acetone. After a further 30 minutes at 0° C., an ice-cooled solution of 6.5 g (0.1 mol) of sodium azide in 15 ml of water is added dropwise. The mixture is stirred for 15 minutes at 0° C. and then worked up using water/toluene.

The toluene phase which has been concentrated to about 50 ml is then added dropwise to a refluxed solution of 3 g (0.04 mol) of tert-butanol and 25 mg (0.15 mmol) of tert-butylcatechol in 20 ml of toluene. The course of the reaction is monitored by means of IR spectroscopy.

The mixture is allowed to cool to room temperature and is concentrated. After separation by column chromatography on silica gel using petroleum ether/ethyl acetate (6 : 1) as the mobile phase, 4 g (30% of theory) of tert-butyl (4-methyl-6-carbomethoxy-2-cyclohexen-1-yl)-carbamate of melting point 89°–91° C. are obtained.

Example A

Phytophthora test (tomato) /protective
Solvent 4.7 parts by weight of acetone
Emulsifier : 0.3 parts by weight of alkyl-aryl polyglycol ether To prepare a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, the plants are inoculated with an aqueous spore suspension of Phytophthora infestans.

The plants are placed in an incubation cabin at 100% relative atmospheric humidity at about 20° C.

The evaluation takes place 3 days after inoculation.

At an active compound concentration of 10 ppm, the degree of effectiveness of compounds 3, 8, 9, 10, 11, 12, 13, 14, 15, 16, 17 and 18 is higher than 90%.

Example B

Pythium sp. test (peas) /seed treatment

The active compounds are applied in the form of agents for dry seed-dressing. They are prepared by extending the active compound in question with ground minerals to give a finely pulverulent mixture which guarantees even distribution on the seed surface.

For the seed dressing, the seeds together with the seed-dressing agent are shaken for 3 minutes in a sealed glass flask.

Seeds are sown at the rate of 2×50 grains in a depth of 2 cm in a naturally Pythium sp.-infected compost soil and grown in a greenhouse at a temperature of about 20° C. in seed boxes which are exposed to the light for 15 hours per day.

The test is evaluated after 14 days.

At a dosage rate of active compound of 250 mg/kg seed, compound 3 shows an outstanding action.

What is claimed is:

1. A substituted cyclohexan-1-yl-amine derivative of the formula

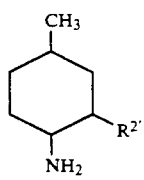

in which

R$^{2'}$ represents the grouping

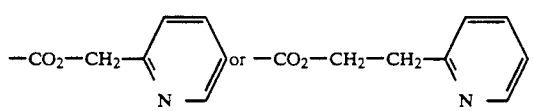

or an acid addition salt or metal salt complex thereof.

2. A compound according to claim 1, wherein such compound is the substituted cyclohexan-1-yl-amine derivative of the formula

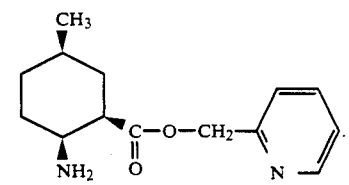

3. A compound according to claim 1, wherein such compound is the substituted cyclohexan-1-yl-amine derivative of the formula

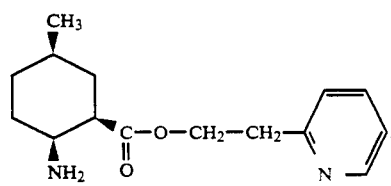

4. A compound according to claim 1, wherein such compound is the substituted cyclohexan-1-yl-amine derivative of the formula

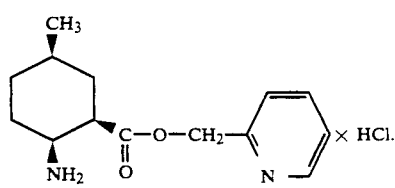

5. A compound according to claim 1, wherein such compound is the substituted cyclohexan-1-yl-amine derivative of the formula

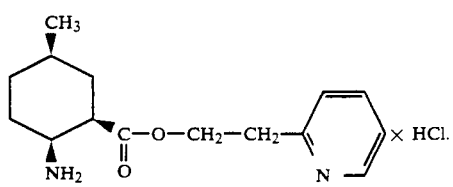

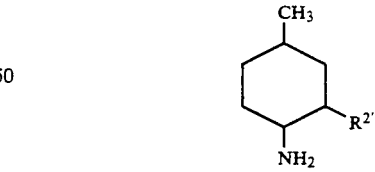

6. A microbicidal composition comprising a microbicidally effective amount of a compound or addition product thereof according to claim 1 and a diluent.

7. A method of combating microbes which comprises applying to such microbes or to a locus from which it is desired to exclude such microbes a microbicidally effective amount of a compound or addition product thereof according to claim 1.

* * * * *